US 6,716,166 B2

(12) United States Patent
Govari (10) Patent No.: US 6,716,166 B2
(45) Date of Patent: Apr. 6, 2004

(54) THREE-DIMENSIONAL RECONSTRUCTION USING ULTRASOUND

(75) Inventor: Assaf Govari, Haifa (IL)

(73) Assignee: Biosense, Inc., New Brunswick, NJ (US)

( * ) Notice: Subject to any disclaimer, the term of this patent is extended or adjusted under 35 U.S.C. 154(b) by 0 days.

(21) Appl. No.: 09/902,087

(22) Filed: Jul. 10, 2001

(65) Prior Publication Data

US 2002/0026118 A1 Feb. 28, 2002

Related U.S. Application Data (60) Provisional application No. 60/226,708, filed on Aug. 18, 2000.

(51) Int. Cl.⁷ ................................................. A61B 8/00
(52) U.S. Cl. .................... 600/437; 600/450; 600/462; 600/466; 600/467
(58) Field of Search ................................ 600/437–472

(56) References Cited

U.S. PATENT DOCUMENTS

| | | | |
|---|---|---|---|
| 4,821,731 A | * 4/1989 | Martinelli et al. ........... 128/916 |
| 4,841,977 A | * 6/1989 | Griffith et al. ............. 29/25.35 |
| 5,078,148 A | * 1/1992 | Nassi et al. ................. 600/455 |
| 5,243,988 A | 9/1993 | Sieben et al. |
| 5,391,199 A | 2/1995 | Ben-Haim |
| 5,398,691 A | * 3/1995 | Martin et al. ............... 600/463 |
| 5,443,489 A | 8/1995 | Ben-Haim |
| 5,577,502 A | * 11/1996 | Darrow et al. .............. 600/426 |
| 5,588,432 A | 12/1996 | Crowley |
| 5,680,860 A | * 10/1997 | Imran ......................... 600/374 |
| 5,730,129 A | * 3/1998 | Darrow et al. .............. 600/407 |
| 5,738,096 A | * 4/1998 | Ben-Haim ................... 128/899 |
| 5,797,849 A | 8/1998 | Vesely et al. |
| 5,846,205 A | 12/1998 | Curley et al. |
| 5,848,969 A | 12/1998 | Panescu et al. |
| 5,876,345 A | 3/1999 | Eaton et al. |
| 5,904,651 A | 5/1999 | Swanson et al. |
| 6,004,269 A | 12/1999 | Crowley et al. |
| 6,059,731 A | 5/2000 | Seward et al. |
| 6,066,096 A | 5/2000 | Smith et al. |
| 6,086,532 A | * 7/2000 | Panescu et al. ............. 600/437 |
| 6,095,976 A | * 8/2000 | Nachtomy et al. .......... 600/443 |
| 6,120,453 A | * 9/2000 | Sharp ......................... 600/463 |
| 6,228,032 B1 | 5/2001 | Eaton et al. |

FOREIGN PATENT DOCUMENTS

| | | |
|---|---|---|
| EP | 945 104 A1 | 9/1999 |
| EP | 0 961 135 A1 | 12/1999 |
| EP | 0 974 936 A2 | 1/2000 |
| GB | 2329708 A | 3/1999 |
| JP | 9 285465 | 4/1996 |
| WO | WO 94/04938 AJ | 3/1994 |
| WO | WO 95 01751 A | 1/1995 |
| WO | WO 96/05768 A1 | 2/1996 |
| WO | WO 97 44089 A | 11/1997 |
| WO | WO 98/18388 A1 | 5/1998 |
| WO | WO 98/46139 A1 | 10/1998 |
| WO | WO 99/55233 A1 | 11/1999 |
| WO | WO 99/58055 A1 | 11/1999 |
| WO | WO 00/19908 A1 | 4/2000 |
| WO | WO 00 23125 A | 4/2000 |

OTHER PUBLICATIONS

Partial European Search Report from correspdoning EP 01 30 6998 dated Dec. 20, 2001.

\* cited by examiner

*Primary Examiner*—Dennis Ruhl
*Assistant Examiner*—William C. Jung
(74) *Attorney, Agent, or Firm*—Louis J. Capezzuto (57) ABSTRACT

Apparatus for mapping a surface of a cavity within a body of a subject includes an elongate probe, having a longitudinal axis and including a distal portion adapted for insertion into the cavity. A plurality of acoustic transducers are distributed along the longitudinal axis over the distal portion of the probe, which transducers are adapted to be actuated individually to emit acoustic waves while the probe is in the cavity, and are further adapted to receive the acoustic waves after reflection of the waves from the surface of the cavity and to generate, responsive to the received waves, electrical signals indicative of times of flight of the waves.

38 Claims, 5 Drawing Sheets

THREE-DIMENSIONAL RECONSTRUCTION USING ULTRASOUND

This application claims the benefit of provisional application No. 60/226,708 filed on Aug. 18, 2000.

FIELD OF THE INVENTION

The present invention relates generally to systems and methods for three-dimensional mapping and reconstruction, and specifically to mapping and reconstruction of the interior of body organs, such as the heart.

BACKGROUND OF THE INVENTION

Methods for three-dimensional geometrical mapping and reconstruction of the endocardial surface are known in the art. For example, U.S. Pat. No. 5,738,096, whose disclosure is incorporated herein by reference, describes methods for mapping the endocardium based on bringing a probe into contact with multiple locations on a wall of the heart, and determining position coordinates of the probe at each of the locations. The position coordinates are combined to form a map of at least a portion of the heart. These methods are effective and accurate, but they require substantial time and skill to carry them out.

A variety of methods have been developed for non-contact reconstruction of the endocardial surface using intracardial ultrasonic imaging. These methods typically use a catheter with a built-in, miniaturized ultrasonic imaging array or scanner. For example, PCT patent publication WO00/19908, whose disclosure is incorporated herein by reference, describes a steerable transducer array for intracardial ultrasonic imaging. The array forms an ultrasonic beam, which is steered in a desired direction by an active aperture. Similarly, U.S. Pat. No. 6,004,269, whose disclosure is also incorporated herein by reference, describes an acoustic imaging system based on an ultrasound device that is incorporated into a catheter. The ultrasound device directs ultrasonic signals toward an internal structure in the heart to create an ultrasonic image.

Further examples of intracardial ultrasonic imaging are presented in U.S. Pat. NO. 5,848,969 and in PCT patent publication WO98/18388, whose disclosures are incorporated herein by reference. These publications describe systems and methods for visualizing interior tissue regions using expandable imaging structures. The structures assume an expanded geometry once inside the heart, which stabilizes an associated imaging probe or array.

U.S. Pat. No. 5,797,849 and PCT patent publication WO99/58055, whose disclosures are also incorporated herein by reference, describe methods for carrying out medical procedures using a three-dimensional tracking and imaging system. The position of a catheter or other probe inside the body is tracked, and its location relative to its immediate surroundings is displayed to improve a physician's ability to precisely position it. Various procedures using such a probe are described in these publications. One such procedure is ultrasonic imaging, using an ultrasound imaging head with transducers held outside the body to image an area inside the body in which a probe with a position sensor is located.

Various methods are known in the art for enhancing ultrasonic images and for extracting information, such as three-dimensional contours, from such images. These methods typically combine information from multiple two-dimensional images to define three-dimensional features. For example, PCT patent publication WO99/55233, whose disclosure is incorporated herein by reference, describes a method for defining a three-dimensional surface of at least a portion of a patient's heart using a plurality of images in different planes. The images are made using an ultrasound transducer at known positions and orientations outside the patient's body. Anatomical landmarks are manually identified in the plurality of images. Other methods of contour extraction and three-dimensional modeling using ultrasonic images are described in European patent application EP 0 961 135 and in Japanese patent application JP 9-285465 whose disclosures are also incorporated herein by reference. As another example, PCT patent publication WO98/46139, whose disclosure is incorporated herein by reference, describes a method for combining Doppler and B-mode ultrasonic image signals into a single image using a modulated nonlinear mapping function.

SUMMARY OF THE INVENTION

It is an object of some aspects of the present invention to provide improved methods and apparatus for three-dimensional mapping and geometrical reconstruction of body cavities, and particularly of chambers of the heart.

In preferred embodiments of the present invention, a cardiac catheter comprises a plurality of acoustic transducers distributed longitudinally along a distal portion of the catheter. The transducers are actuated individually, in sequence, to emit acoustic waves, preferably ultrasonic waves, while the catheter is inside a chamber of the heart. The acoustic waves are reflected from the endocardial surface of the cavity and are received by the transducers. Processing circuitry, coupled to the transducers, determines the times of flight of the received acoustic waves, thus providing a measurement of the distance from each of the transducers to a point or area on the endocardial surface opposite the transducer. The distance measurements are combined to reconstruct the three-dimensional shape of the surface, which is preferably displayed in the form of a geometrical map.

Preferred embodiments of the present invention thus enable the entire endocardial surface to be mapped rapidly, typically within a single heart beat. This rapid mapping can be achieved because the acoustic waves are used to measure three-dimensional distances directly, rather than attempting to image the heart and then extract geometrical information from the images as in methods known in the art. The distance measurements are facilitated by the unique design of the catheter, wherein the transducers are distributed longitudinally along the catheter, instead of being concentrated in a phased array or other imaging configuration. Preferred embodiments of the present invention also avoid the need for physical contact between the catheter and the endocardial surface during measurement.

In some preferred embodiments of the present invention, the catheter comprises one or more position sensors, which are used to determine position and orientation coordinates of the catheter within the heart. Using the position sensors in conjunction with the acoustic measurements allows the reconstructed three-dimensional shape of the surface to be located and oriented in space. It also enables multiple measurements to be taken at different positions within the heart in order to enhance the accuracy of the reconstruction. Preferably, the position sensors comprise one or more miniature coils, which are used to determine position and orientation coordinates by transmitting or receiving electromagnetic waves, as described, for example, in PCT patent publication WO96/05768 or in U.S. Pat. No. 5,391,199, which are incorporated herein by reference. Alternatively, the acoustic transducers on the catheter also serve as position sensors, by receiving acoustic waves transmitted from a plurality of acoustic transducers at fixed positions outside the body, or by transmitting acoustic waves to these external transducers. The times of flight of these waves are used to determine the position and orientation of the catheter. Further alternatively, other types of position sensing systems, as are known in the art, may be used.

In further preferred embodiments of the present invention, the catheter comprises a plurality of electrodes in addition to the acoustic transducers, and is used for electrical, as well as geometrical, mapping of the heart. Preferably, the electrical mapping is performed rapidly using an array of non-contact electrodes, most preferably as described in a U.S. patent application entitled "Rapid Mapping of Electrical Activity in the Heart," filed Jun. 21, 2000 (applicant's docket no. BIO 97 US), which is assigned to the assignee of the present patent application and is incorporated herein by reference. The electrical and geometrical maps are registered to provide an integrated view of mechanical and electrical properties of the heart.

In some preferred embodiments of the present invention, other features of the acoustic waves received by the transducers on the catheter are analyzed to provide further geometrical and diagnostic information. For example, in one such embodiment, the processing circuitry analyzes the reflected waves to find reflections from both the endocardial and the epicardial surfaces. In this manner, both of the surfaces can be reconstructed simultaneously, and the thickness of the heart wall can be mapped.

In another embodiment, the processing circuitry analyzes the frequency, as well as the time of flight, of the reflected waves in order to detect a Doppler shift. The Doppler measurement is used to determine and map the heart wall velocity. This method thus enables the relative speeds of opposing or mutually-perpendicular segments of the heart wall to be measured simultaneously. By contrast, methods of echo Doppler measurement known in the art use a probe outside the body and therefore can measure wall velocity of only one side of the heart at any given time.

Although preferred embodiments are described herein with reference to cardiac catheters for mapping chambers of the heart, other applications of the present invention will be apparent to those skilled in the art. These applications include, but are not limited to, mapping and geometrical reconstruction of other body cavities, such as the coronary arteries or the gastrointestinal system.

There is therefore provided, in accordance with a preferred embodiment of the present invention, apparatus for mapping a surface of a cavity within a body of a subject, including:

an elongate probe, having a longitudinal axis and including a distal portion adapted for insertion into the cavity; and a plurality of acoustic transducers, distributed along the longitudinal axis over the distal portion of the probe, which transducers are adapted to be actuated individually to emit acoustic waves while the probe is in the cavity, and are further adapted to receive the acoustic waves after reflection of the waves from the surface of the cavity and to generate, responsive to the received waves, electrical signals indicative of times of flight of the waves.

Preferably, the cavity includes a chamber of the heart of the subject, and the probe includes an intracardiac catheter.

Additionally or alternatively, the probe includes a position sensor, which is adapted to generate signals indicative of position coordinates of the probe within the body. Preferably, the position sensor includes a coil, and wherein the signals include electrical currents induced in the coil by an externally-applied magnetic field.

Preferably, the apparatus includes control circuitry, adapted to actuate the transducers sequentially and to receive and to process the electrical signals generated by the transducers so as to reconstruct a three-dimensional shape of the surface of the cavity based on the times of flight. Further preferably, responsive to the times of flight, the circuitry is adapted to determine distances from the transducers to respective points on the surface of the cavity opposite the transducers, and to combine the determined distances so as to reconstruct the shape. Additionally or alternatively, the circuitry is operative to distinguish the signals generated responsive to the waves that have undergone one reflection from the surface of the cavity from the signals generated responsive to the waves that have undergone multiple reflections, and to reject the signals due to the waves that have undergone the multiple reflections.

Preferably, the cavity has a wall, and the surface includes an inner surface of the wall and an outer surface of the wall, and the circuitry is adapted to distinguish the signals generated responsive to the waves that have been reflected from the inner surface from the signals generated responsive to the waves that have been reflected from the outer surface. In a preferred embodiment, the circuitry is operative to determine a thickness of the wall responsive to the signals generated by the waves that have been reflected from the inner surface and the waves that have been reflected from the outer surface.

In another preferred embodiment, the circuitry is adapted to detect a spectral shift in the acoustic waves received by the transducer and to determine, responsive to the spectral shift, a velocity of motion of the surface.

In still another preferred embodiment, the apparatus includes one or more electrodes disposed on the distal portion of the probe, which are adapted to convey electrical signals to the circuitry responsive to electrical activity in the cavity, wherein the circuitry is adapted, responsive to the signals from the electrodes, to superimpose an indication of the electrical activity on the three-dimensional shape of the surface. Preferably, the indication of the electrical activity includes a map of electrical potentials at the surface of the cavity, which is registered with the three-dimensional shape of the surface. Preferably, the apparatus includes a display, which is driven by the circuitry to display an image of the three-dimensional shape.

In a preferred embodiment, the apparatus includes a plurality of reference transducers outside the body, which are adapted to transmit acoustic waves into the body, such that the waves are received by the transducers on the probe, causing the transducers to generate electrical reference signals, and the circuitry is adapted to process the reference signals so as to determine position coordinates of the probe. Preferably, responsive to the determined position coordinates, the circuitry is adapted to define a position of the three-dimensional shape within the body.

In a preferred embodiment, the apparatus includes one or more electrodes disposed on the distal portion of the probe, which are adapted to detect electrical activity in the cavity, wherein the electrical activity detected by the one or more electrodes includes varying electrical potentials at the surface of the cavity. Preferably, the one or more electrodes include an array of non-contact electrodes, which are adapted to detect the varying electrical potentials at the surface substantially without making contact with the surface.

There is also provided, in accordance with a preferred embodiment of the present invention, a method for mapping a surface of a cavity within a body of a subject, including:

inserting a probe into the cavity, the probe having a longitudinal axis; sequentially emitting acoustic waves within the cavity from each of a plurality of points distributed along the longitudinal axis of the probe;

receiving the acoustic waves at the points following reflection of the emitted waves from the surface of the cavity;

analyzing the received waves to determine times of flight of the waves; and reconstructing a three-dimensional shape of the surface of the cavity based on the determined times of flight.

Preferably, the method includes determining position coordinates of the probe inside the body, wherein reconstructing the three-dimensional shape includes reconstructing the shape responsive to the coordinates, and wherein reconstructing the shape includes defining a position of the shape inside the body using the coordinates. Additionally or alternatively, emitting and receiving the waves include emitting and receiving the waves at a plurality of different locations of the probe in the cavity, and reconstructing the shape includes reconstructing the shape based on the waves received at the different locations, using the coordinates of the probe determined at the different locations.

Alternatively, emitting and receiving the waves include emitting and receiving the waves while the probe is held substantially stationary at a single location in the cavity, and reconstructing the three-dimensional shape includes reconstructing the shape based substantially only on the waves received at the single location.

In a preferred embodiment, the method includes sensing electrical activity in the cavity using electrical sensors on the probe, wherein reconstructing the shape includes superimposing an indication of the electrical activity on the reconstructed three-dimensional shape of the surface.

The present invention will be more fully understood from the following detailed description of the preferred embodiments thereof, taken together with the drawings in which:

DETAILED DESCRIPTION OF PREFERRED EMBODIMENTS

Figure 1:
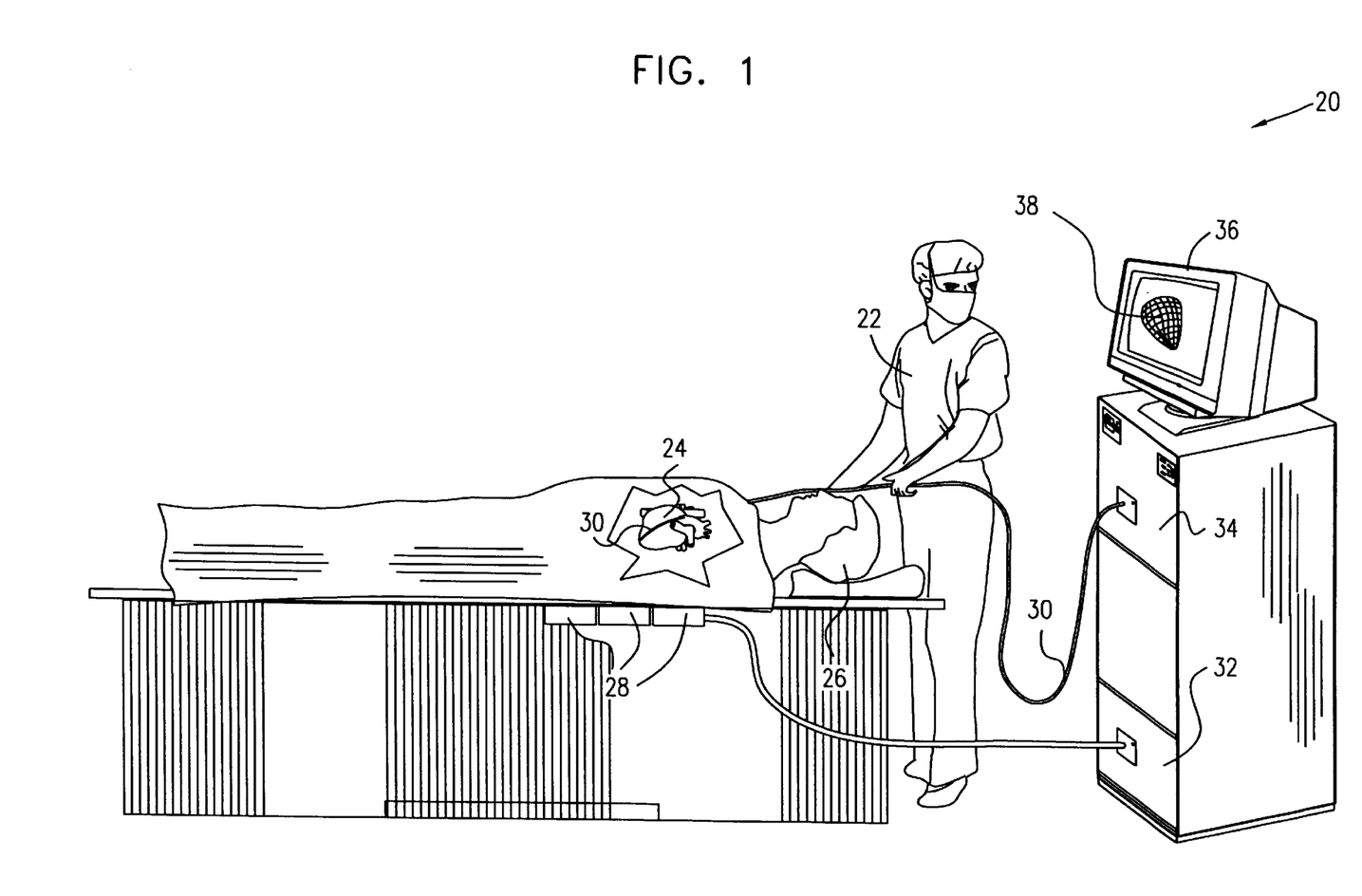
FIG. 1 is a schematic, pictorial illustration of a system for geometrical mapping of the heart, in accordance with a preferred embodiment of the present invention.

FIG. 1 is a schematic, pictorial illustration of a mapping system 20, for three-dimensional geometrical mapping of a heart 24 of a subject 26, in accordance with a preferred embodiment of the present invention. System 20 comprises an elongate probe, preferably a catheter 30, which is inserted by a user 22 through a vein or artery of the subject into a chamber of the heart.

Figure 2:
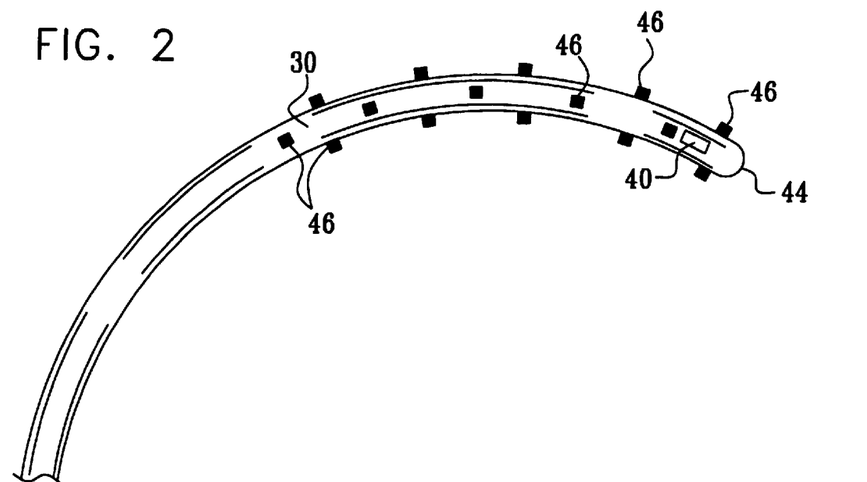
FIG. 2 is a schematic, pictorial illustration of a distal portion of a catheter for use in the system of FIG. 1, in accordance with a preferred embodiment of the present invention.

FIG. 2 is a schematic, pictorial illustration showing a distal portion of catheter 30, which is inserted into heart 24. The catheter has an array of ultrasonic transducers 46 on its outer surface, preferably ten to twenty such transducers, each about 0.5 mm in size, arrayed longitudinally along the catheter proximal to a distal end 44 thereof. Optionally, the catheter may also comprise electrodes, as described below, and other diagnostic and therapeutic features (not shown in the figures), as are known in the art.

Catheter 30 preferably comprises a position sensor 40, most preferably located near distal tip 44. Alternatively, one or more additional position sensors are deployed in the catheter, preferably near a proximal end of the array of transducers. Sensor 40 preferably comprises an electromagnetic sensor, which is mounted within the catheter by any suitable method, for example, using polyurethane glue or the like. The sensor is electrically connected to an electromagnetic sensor cable (not shown), which extends through the catheter body and into a control handle of the catheter. The electromagnetic sensor cable comprises multiple wires encased within a plastic covered sheath. Within the catheter body, the sensor cable may be enclosed within a protective sheath along with lead wires of transducers 46, if desired. In the control handle, the wires of the sensor cable are connected to a circuit board (not shown), which amplifies the signals received from the electromagnetic sensor and transmits them to a computer housed in a console 34 (FIG. 1), in a form understandable to the computer. Also, because the catheter is designed for single use only, the circuit board preferably contains an EPROM chip, which shuts down the circuit board after the catheter has been used. This prevents the catheter, or at least the electromagnetic sensor, from being used twice.

A suitable electromagnetic sensor is described, for example, in U.S. Pat. No. 5,391,199, which is incorporated herein by reference. A preferred electromagnetic mapping sensor is manufactured by Biosense Ltd. (Tirat Hacarmel, Israel) and marketed under the trade designation NOGA.

To use the electromagnetic sensor, the patient is placed in a magnetic field generated, for example, by situating under the patient a pad containing field generator coils 28 for generating a magnetic field. A reference electromagnetic sensor (not shown) is preferably fixed relative to the patient, e.g., taped to the patient's back, and catheter 30 containing sensor 40 is advanced into the patient's heart 24. The sensor preferably comprises three small coils which in the magnetic field generate weak electrical signals indicative of their position in the magnetic field. Signals generated by both the fixed reference sensor and by sensor 40 in the heart are amplified and transmitted to console 34, which analyzes the signals and then displays the signals on a monitor 36. By this method, the precise location of the sensor in the catheter relative to the reference sensor can be ascertained and visually displayed. The sensors can also detect displacement of that catheter that is caused by contraction of the heart muscle.

Some of the features of catheter 30 and system 20 are implemented in the NOGA-STAR catheter marketed by Biosense Webster, Inc., and in the above-mentioned Biosense-NOGA system, also marketed by Biosense Webster, Inc. Further aspects of the design of catheter 30 and of system 20 generally are described in U.S. patent application Ser. No. 09/506,766, which is assigned to the assignee of the present patent application and is incorporated herein by reference. The detailed design of catheter 30 and the geometrical and electrical mapping functions carried out using the catheter and system 20, however, as described hereinbelow, are unique to the present invention.

As noted above, sensor 40 preferably comprises three non-concentric coils, such as those described in the above-mentioned PCT patent publication WO96/05768. The coils sense magnetic fields generated by field generator coils 28, which are driven by driver circuits 32 (FIG. 1). Alternatively, the sensors may generate fields, which are detected by coils 28. System 20 thus achieves continuous generation of six dimensions of position and orientation information with respect to sensor 40. Alternatively, sensor 40 (and, optionally, additional position sensors in catheter 30) may comprise a single coil, which is sufficient, in conjunction with field generator coils 28, to generate three dimensions of position and two dimensions of orientation information. The third dimension of orientation (typically rotation of catheter 30 about its longitudinal axis) can be inferred if needed from a comparison of the coordinates of two such sensors provided at mutually-spaced locations in the catheter and/or from mechanical information.

Further alternatively, the sensors may comprise other types of position and/or coordinate sensors, as described, for example, in U.S. Pat. Nos. 5,391,199 or 5,443,489 or in PCT publication WO 94/04938, or substantially any other suitable type of position/coordinate sensing device known in the art. Still further alternatively or additionally, catheter 30 is marked with one or more markers whose positions can be determined from outside of the body, such as radio-opaque markers for use with a fluoroscope.

As noted above, catheter 30 is coupled to console 34, which enables the user to observe and regulate the functions of the catheter. Console 34 includes a processor, preferably a computer with appropriate signal processing circuits (which are typically contained inside a housing of the computer). The processor is coupled to drive display 36. The signal processing circuits typically generate drive signals, causing each of transducers 46 to emit ultrasonic pulses in sequence. The circuits further receive, amplify, filter and digitize signals from catheter 30, including signals generated by position sensor 40 and transducers 46. The digitized signals are received and used by the console to compute the position and orientation of the catheter and to extract the times of flight of the acoustic waves within the heart. The information derived from this analysis is used to reconstruct a three-dimensional geometrical map 38 of the endocardial surface of heart 24.

Typically, system 20 includes other elements, which are not shown in the figures for the sake of simplicity. Some of these elements are described, for example, in U.S. patent application Ser. No. 09/122,137, which is assigned to the assignee of the present patent application, and whose disclosure is incorporated herein by reference. For instance, system 20 may include an ECG monitor, coupled to receive signals from one or more body surface electrodes, so as to provide an ECG synchronization signal to console 34. As mentioned above, the system typically also includes a reference position sensor, either on an externally-applied reference patch attached to the exterior of the patient's body, or on an internally-placed catheter, which is inserted into heart 24 and maintained in a fixed position relative to the heart. By comparing the position of catheter 30 to that of the reference catheter, the coordinates of catheter 30 are accurately determined relative to the heart, irrespective of heart motion. Alternatively, any other suitable method may be used to compensate for heart motion.

Figure 3:
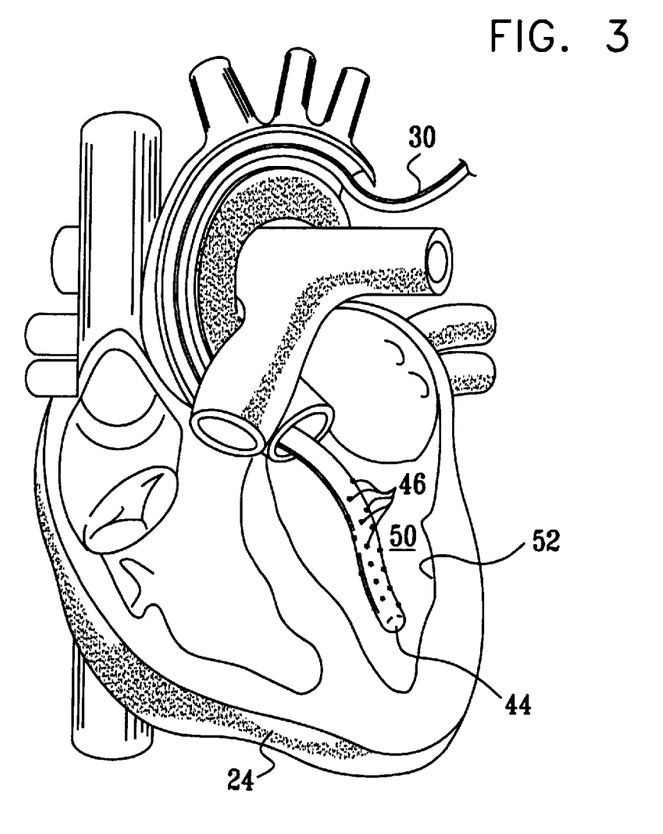
FIG. 3 is a schematic, cutaway illustration of a heart into which the catheter of FIG. 2 has been inserted, in accordance with a preferred embodiment of the present invention.

FIG. 3 is a schematic, sectional illustration of heart 24, showing the distal portion of catheter 30 inserted through the aorta into a left ventricle 50 of the heart, in accordance with a preferred embodiment of the present invention. Transducers 46 are driven by console 34 to emit ultrasonic waves toward endocardium 52. The transducers receive the waves reflected back from the heart wall and generate electrical signals, which are conveyed to console 34 for processing and analysis. There is no need for tip 44 or for any other portion of catheter 30 to contact the endocardium during the ultrasonic measurements.

Figure 4:
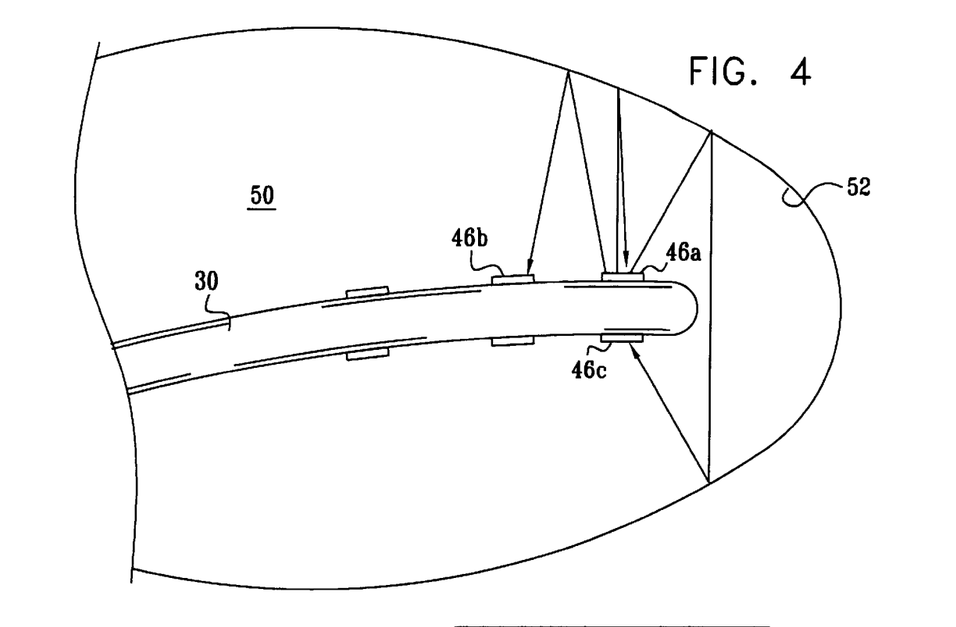
FIG. 4 is a schematic detail of the heart and catheter of FIG. 3, illustrating reflections of acoustic waves from an inner surface of a heart chamber, in accordance with a preferred embodiment of the present invention.
Figure 5:
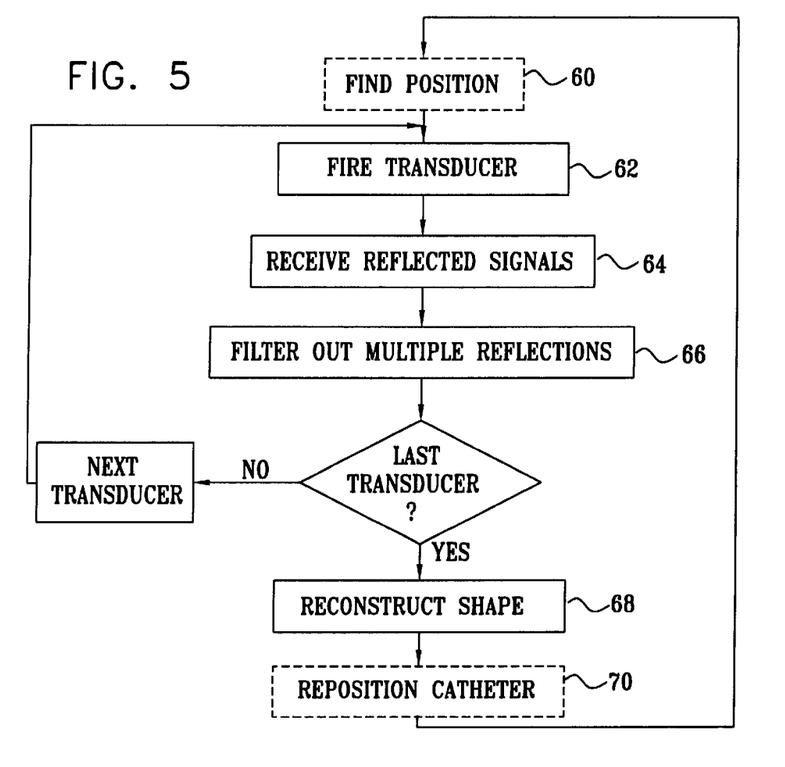
FIG. 5 is a flow chart that schematically illustrates a method for generating a three-dimensional reconstruction of the inner surface of the heart, in accordance with a preferred embodiment of the present invention.

Reference is now made to FIGS. 4 and 5, which schematically illustrate a method for three-dimensional geometrical mapping and reconstruction of ventricle 50, in accordance with a preferred embodiment of the present invention. FIG. 4 shows a detail of catheter 30 inside the ventricle, in which a number of transducers 46 are labeled 46a, 46b and 46c, for the purpose of the description below. FIG. 5 is a flow chart that details the steps in the method. Although this method is described with reference to mapping of left ventricle 50, it will be appreciated that it is similarly applicable to mapping other chambers of heart 24, as well as to mapping of other body cavities.

At a positioning step 60, catheter 30 is inserted into ventricle 50 and is positioned in a desired location and orientation by user 22. Preferably, position sensor 40 is used to determine position and orientation coordinates of the distal portion of the catheter inside the heart, as described above. Alternatively, however, position sensing may be omitted, and endocardium 52 may be geometrically reconstructed without a specific position reference. Such position-independent reconstruction is possible as long as all of the necessary signals are collected from transducers 46 within a period short enough so that the heart can be considered to be stationary during the measurement, i.e., in a space of time considerably shorter than a single heart beat. Such rapid measurement is feasible using system 20, as described in greater detail hereinbelow.

At a transducer firing step 62, a first one of the transducers on catheter 30, say transducer 46a, is actuated by a signal from console 34. The actuation causes the transducer to emit an ultrasonic pulse, preferably at a frequency of about 5–9 MHz and with a duration of about 1 $\mu$s. The emitted ultrasonic waves preferably form a beam having a narrow divergence angle, preferably less than 20°, and most preferably about 3°. The beam impinges on an area that is about 4 mm in diameter on endocardium 52, in a location that is perpendicularly opposite transducer 46a. The size of the beam on the endocardium is determined by the distance of the transducer from the endocardium, which will typically be about 2–3 cm, depending on the dimensions of the heart.

The waves emitted by transducer 46a bounce off the inner surface of endocardium 52 and are reflected back to transducer 46a and to other transducers on catheter 30. Assuming the reflection to include both diffuse and specular components, the reflected energy will largely be concentrated on transducer 46a and on its near neighbors, such as transducer 46b, as shown in FIG. 4. These waves are received by transducers 46, at a reflection reception step 64, generating electrical signals that are processed by console 34. The console finds the time of flight of the waves received at each of the transducers by comparing the arrival time of the electrical signals to the actuation time of transducer 46a. This time of flight is proportional to the length of the path traversed to endocardium 52 and back to transducer 46a or 46b. The path length thus determined from the time-of-flight information is used in reconstructing the geometrical shape of ventricle 50, as described below. Based on the size of the typical heart, the time of flight is generally less than 50 μs.

The ultrasonic waves emitted by transducer 46a are most strongly reflected from endocardium 52, i.e., from the inner surface of ventricle 50. There may also be reflections, however, from the epicardium of the ventricle and from other structures in proximity to the ventricle. Therefore, to determine the time of flight at step 64, console 34 preferably measures the arrival time of the first strong peak in the signals generated by the transducers upon receiving the reflected waves. This peak corresponds to reflection from endocardium 52. Optionally, the console may also detect and measure the arrival time of a second peak in each signal, which typically corresponds to reflection from the epicardium. The difference between the arrival times of the first and second peaks gives a measure of the local thickness of the heart wall.

As a further option, console 34 determines not only the arrival times of the reflected waves at transducers 46, but also finds frequency spectra of the waves, as is known in the art. If the heart wall is moving toward or away from transducer 46a at the time the transducer is actuated, the reflected waves will undergo a Doppler shift. The frequency spectra will therefore indicate the velocity of the heart wall relative to the catheter. Console 34 preferably analyzes this spectral information, in conjunction with the distance information provided by the time of flight, in order to measure the wall velocity.

Multiple reflections within ventricle 50 may also occur, as illustrated, for example, by the two-bounce path from transducer 46a to transducer 46c shown in FIG. 4. The path length measured in this case for the waves received at transducer 46c will therefore provide confusing geometrical information regarding ventricle 50 and should be ignored. To avoid being confused by multiple-bounce signals, console 34 rejects the signal received from transducer 46c, at a multiple reflection filtering step 66. Such signals are preferably detected by setting a maximum time of flight from transducer 46a to any other transducer, and discarding measurements in excess of this maximum.

The process of steps 62, 64 and 66 is repeated by actuating the next transducer 46 in sequence, say transducer 46b. The repetition continues until a sufficient number of transducers 46 have been actuated, and the resulting reflected waves have been received and times of flight determined. Considering the short times of flight of the waves, all of the ten or twenty transducers 46 can be actuated in succession within no more than about 10 ms. Alternatively, two or more of the transducers may be actuated simultaneously, as long as the acoustic signals that they generate are distinguishable, by differences in frequency, for example. Whether the transducers are actuated sequentially or simultaneously, it is possible to measure distances from the transducers to a large number of points distributed over all or a substantial portion of endocardium 52, within a time considerably less than a single heart beat.

At a shape reconstruction step 68, console 34 combines the distance data deduced from the measured times of flight to build a three-dimensional geometrical map of ventricle 52. Each time of flight gives a distance and a direction from the receiving transducer on catheter 30 that generated the signal to a point on the endocardial surface determined by the locations of the transmitting and the receiving transducer. If position sensor 40 is used, the distance and direction can be used to determine absolute coordinates of the point of the endocardial surface. Otherwise, the coordinates of the point are found in a frame of reference determined arbitrarily by the (unknown) position of the catheter. In either case, all of the points from all of the measurements are placed in a three-dimensional space, and a surface is fitted to the points in order to generate map 38. Preferably, the reconstruction is carried out using methods described in European patent application EP 0 974 936 or the above-mentioned U.S. patent application Ser. No. 09/122,137. Alternatively, other methods of geometrical reconstruction may be used, as are known in the art.

Optionally, for greater accuracy, catheter 30 is repositioned, at a repositioning step 70, and steps 60 through 68 are repeated. Preferably, the additional points on the endocardial surface that are found at this step are used to refine and correct map 38 that was generated in the preceding iteration. Measurements at multiple different positions of the catheter may be carried out and combined in this manner.

To the extent that console 34 gathered other information in conjunction with finding the times of flight, this information is preferably shown in map 38, as well. For example, the map may show both endocardial and epicardial surfaces, preferably with the option of showing a sectional view in a desired plane through the heart to allow the wall thickness to be visualized. If Doppler measurements are made, the map preferably shows the wall velocity as a function of position, by color coding, for example. The velocity information may be used to calculate a measure of the heart's contraction strength or efficiency. The geometrical map may also display electrical information, as described below.

Figure 6:
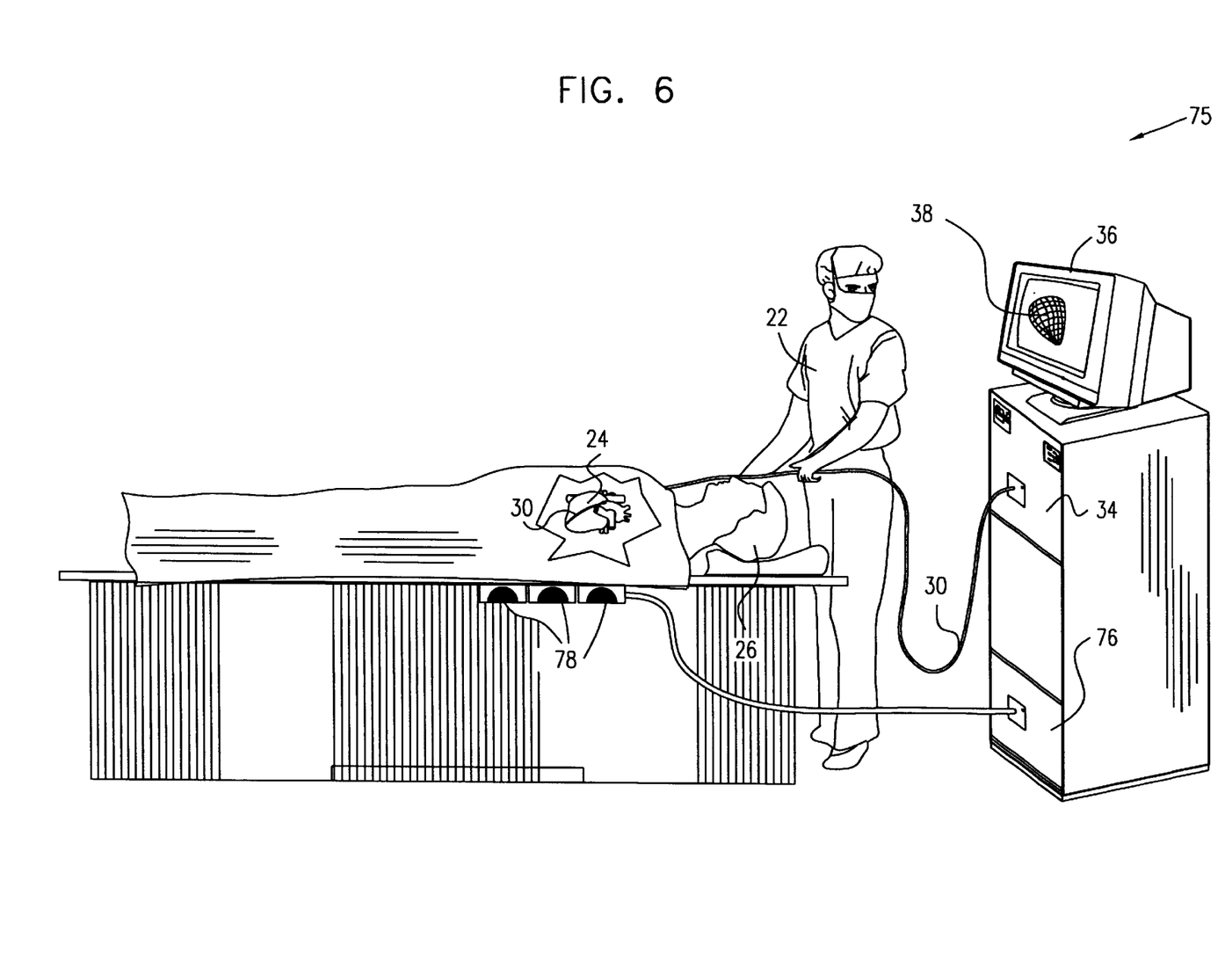
FIG. 6 is a schematic, pictorial illustration of a system for geometrical mapping of the heart, in accordance with another preferred embodiment of the present invention.

FIG. 6 is a schematic, pictorial illustration of a system 75 for geometrical mapping of heart 24, in accordance with another preferred embodiment of the present invention. System 75 is substantially identical to system 20, shown in FIG. 1 and described hereinabove, except for its mode of determining the position of catheter 30 inside heart 24. In place of magnetic position determination using sensor 40 in catheter 30, system 75 uses transducers 46 on catheter 30 to determine the catheter's position ultrasonically.

For this purpose, a number of ultrasonic transmitters 78, preferably having a generally spherical or hemispherical shape, are positioned outside the body of patient 26 and irradiate the vicinity of heart 24 with ultrasonic waves. In the present embodiment, the transmitters are positioned under the patient's back. Transmitters 78 are preferably driven in sequence by an ultrasonic driver 76 to emit their ultrasonic waves. The waves are received by transducers 46 on catheter 30, and the times of flight of the waves are measured to determine the distances between selected points on the catheter and the known locations of the transmitters. (Alternatively, transducers 46 may emit signals, to be detected by fixed receivers outside the body, in place of transmitters 78.) The distances are triangulated to find position coordinates of the catheter in the heart.

Thus, in the embodiment of FIG. 6, transducers 46 serve as both position sensors and mapping detectors. Consequently, system 75 will generally be lower in cost than system 20. Although magnetic position sensing is typically more accurate than ultrasonic position sensing, the ultrasonic sensing mode of the present embodiment is adequate for most applications of the system, since it is necessary to determine only relative positions of catheter 30 and heart 24, and not absolute positions.

Figure 7:
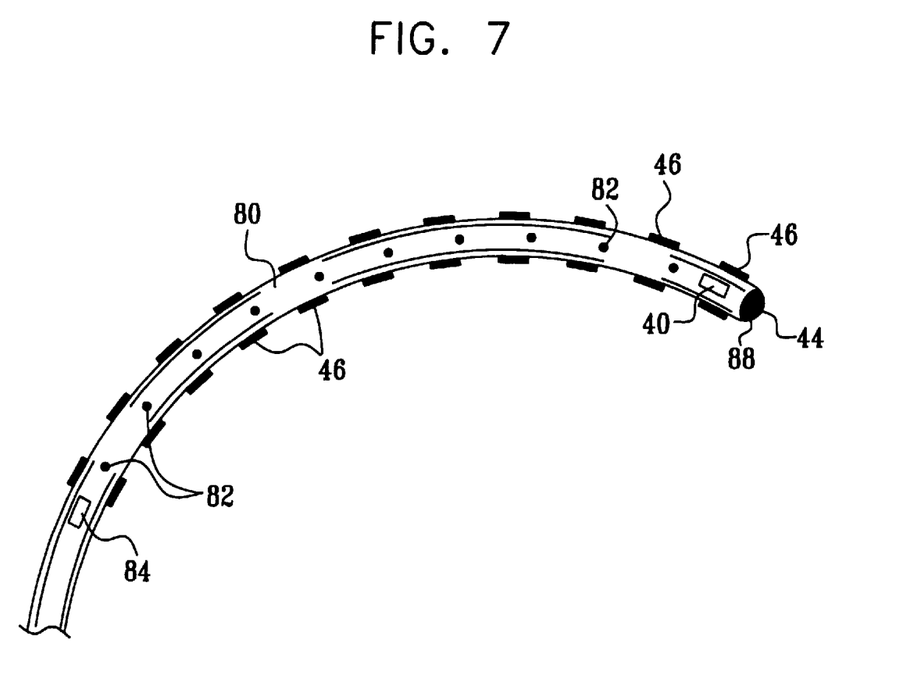
FIG. 7 is a schematic, pictorial illustration of a distal portion of a catheter for use in geometrical and electrical mapping of the heart, in accordance with a preferred embodiment of the present invention.

FIG. 7 is a schematic, pictorial illustration of a catheter 80 for use in system 20 or system 75, in accordance with still another preferred embodiment of the present invention. Catheter 80 is largely similar to catheter 30, but is also adapted to make electrophysiological measurements, in conjunction with the geometrical mapping functions described in detail hereinabove. For this purpose, catheter 80 comprises, in addition to transducers 46, an array of non-contact electrodes 82, distributed proximally to distal end 44 of the catheter. These electrodes are preferably used to perform rapid electrical mapping of endocardium 52, most preferably as described in the above-mentioned U.S. patent application entitled "Rapid Mapping of Electrical Activity in the Heart." Alternatively or additionally, catheter 80 comprises one or more contact electrodes 88. Preferably, an additional position sensor 84 is provided, so that the positions of all of electrodes 82 can be accurately determined.

In operation, console 34 receives both acoustic signals from transducers 46 and electrical signals from electrodes 82. The acoustic signals are used to reconstruct the three-dimensional geometrical shape of ventricle 50, as described above. The console uses this geometrical information, together with the electrical signals, to generate a three-dimensional map of electrical potentials at surface 52 of the ventricle. The electrical map is preferably superposed on geometrical map 38, in the form of contour lines or color coding, for example, in order to provide an integrated, electrical and mechanical picture of the ventricle.

This rapid acoustical and electrical mapping using non-contact transducers 46 and electrodes 82 may be supplemented with contact measurements for enhanced accuracy at particular points. For example, an optional electrode 88 at the distal tip of catheter 80 may be brought into contact with points on the endocardium to measure electrical potentials at these points. Meanwhile, position sensor 40 provides an accurate reading of the position coordinates of electrode 88. Additional data points gathered in this manner are preferably marked on map 38. Alternatively, electrode 88 may be driven to ablate areas of the endocardial surface in order to treat arrhythmias detected in an earlier mapping stage, for example. Other modes of therapy, as are known in the art, may also be administered by a suitably-configured catheter, in conjunction with the mapping and reconstruction functions provided by the present invention.

Although preferred embodiments are described herein with reference to cardiac catheters 30 and 75, for mapping chambers of heart 24, other applications of the principles of the present invention will be apparent to those skilled in the art. These applications include, but are not limited to, mapping and geometrical reconstruction of other body cavities, such as the coronary arteries or the gastrointestinal system.

It will thus be appreciated that the preferred embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

What is claimed is:

1. Apparatus for mapping a surface of a cavity within a body of a subject, comprising:
    an elongate probe, having a longitudinal axis and comprising a distal portion adapted for insertion into the heart and a probe position sensor, which is adapted to generate signals indicative of position coordinates of the probe within the body;
    a plurality of acoustic transducers, distributed along the longitudinal axis over the distal portion of the probe, which transducers are adapted to be actuated individually to emit acoustic waves while the probe is in the heart, and are further adapted to receive the acoustic waves after reflection of the waves from the surface of the heart and to generate, responsive to the received waves, electrical signals indicative of times of flight of the waves;
    a reference position sensor maintained in a fixed position relative to the body of the subject;
    signal processing circuitry for receiving the electrical signals indicative of times of flight of the waves from the acoustic transducers and for receiving the signals indicative of position coordinates of the probe from the probe position sensor for reconstructing a three-dimensional geometric map of the surface of the heart, the signal processing circuitry also comparing the signals indicative of position coordinates of the probe to the fixed position of the reference position sensor for determining a position of the probe position sensor which accounts for motion of the heart.

2. Apparatus according to claim 1, wherein the probe comprises an intracardiac catheter.

3. Apparatus according to claim 1, wherein the probe position sensor comprises a coil, and wherein the signals comprise electrical currents induced in the coil by an externally-applied magnetic field.

4. Apparatus according to claim 1, wherein the signal processing circuitry actuate the transducers sequentially.

5. Apparatus according to claim 4, wherein responsive to the times of flight, the circuitry is adapted to determine distances from the transducers to respective points on the surface of the heart opposite the transducers, and to combine the determined distances so as to reconstruct the surface of the heart.

6. Apparatus according to claim 4, wherein the circuitry is operative to distinguish the signals generated responsive to the waves that have undergone one reflection from the surface of the heart from the signals generated responsive to the waves that have undergone multiple reflections, and to reject the signals due to the waves that have undergone the multiple reflections.

7. Apparatus according to claim 4, wherein the heart has a wall, and the surface comprises an inner surface of the wall and an outer surface of the wall, and wherein the circuitry is adapted to distinguish the signals generated responsive to the waves that have been reflected from the inner surface from the signals generated responsive to the waves that have been reflected from the outer surface.

8. Apparatus according to claim 7, wherein the circuitry is operative to determine a thickness of the wall responsive to the signals generated by the waves that have been reflected from the inner surface and the waves that have been reflected from the outer surface.

9. Apparatus according to claim 4, wherein the circuitry is adapted to detect a spectral shift in the acoustic waves received by the transducer and to determine, responsive to the spectral shift, a velocity of motion of the surface.

10. Apparatus according to claim 4, and comprising one or more electrodes disposed on the distal portion of the probe, which are adapted to convey electrical signals to the circuitry responsive to electrical activity in the heart, wherein the circuitry is adapted, responsive to the signals from the electrodes, to superimpose an indication of the electrical activity on the three-dimensional geometrical map of the surface.

11. Apparatus according to claim 10, wherein the indication of the electrical activity comprises a map of electrical potentials at the surface of the heart, which is registered with the three-dimensional geometrical map of the surface.

12. Apparatus according to claim 4, and comprising a display, which is driven by the circuitry to display an image of the three-dimensional geometrical map of the surface.

13. Apparatus according to claim 4, and comprising a plurality of reference transducers outside the body, which are adapted to transmit acoustic waves into the body, such that the waves are received by the transducers on the probe, causing the transducers to generate electrical reference signals, and wherein the circuitry is adapted to process the reference signals so as to determine position coordinates of the probe.

14. Apparatus according to claim 13, wherein responsive to the determined position coordinates, the circuitry is adapted to define a position of the surface within the body.

15. Apparatus according to claim 1, and comprising one or more electrodes disposed on the distal portion of the probe, which are adapted to detect electrical activity in the heart.

16. Apparatus according claim 15, wherein the electrical activity detected by the one or more electrodes comprises varying electrical potentials at the surface of the heart.

17. Apparatus according to claim 16, wherein the one or more electrodes comprise an array of non-contact electrodes, which are adapted to detect the varying electrical potentials at the surface substantially without making contact with the surface.

18. A method for mapping a surface of a heart within a body of a subject, comprising:

providing an elongate probe, having a longitudinal axis and comprising a distal portion adapted for insertion into the heart and a probe position sensor, which is adapted to generate signals indicative of position coordinates of the probe within the body; and a plurality of acoustic transducers, distributed along the longitudinal axis over the distal portion of the probe, which transducers are adapted to be actuated individually to emit acoustic waves while the probe is in the heart, and are further adapted to receive the acoustic waves after reflection of the waves from the surface of the heart and to generate, responsive to the received waves, electrical signals indicative of times of flight of the waves;

maintaining a reference position sensor in a fixed position relative to the body of the subject;

inserting the probe into the heart and sequentially emitting acoustic waves within the cavity from each of the plurality of the acoustic transducers;

receiving the acoustic waves at the transducers following reflection of the emitted waves from the surface of the heart;

generating electrical signals indicative of times of flight of the waves;

analyzing the electrical signals indicative of times of flight of the waves and the signals indicative of position coordinates of the probe to include comparing the signals indicative of position coordinates of the probe to the fixed position of the reference position sensor and determining a position of the probe position sensor which accounts for motion of the heart; and reconstructing a three-dimensional geometrical map of the surface of the heart based on the determined times of flight and the position of the probe position sensor which accounts for motion of the heart.

19. A method according to claim 18, wherein the surface of the heart is within a chamber of the heart of the subject, and the probe comprises an intracardiac catheter.

20. A method according to claim 18, wherein reconstructing the geometrical map comprises defining a position of a shape of the surface of the heart inside the body using the coordinates.

21. A method according to claim 18, wherein emitting and receiving the waves comprise emitting and receiving the waves at a plurality of different locations of the probe in the heart, and wherein reconstructing the geometrical map comprises reconstructing the shape of the surface of the heart based on the waves received at the different locations, using the coordinates of the probe determined at the different locations.

22. A method according to claim 18, wherein the position sensor comprises a coil, and wherein determining the coordinates comprises detecting electrical current induced in the coil by an externally-applied magnetic field.

23. A method according to claim 18, wherein determining the position coordinates comprises transmitting and receiving reference acoustic waves between reference points outside the body and the points on the probe, and analyzing the received reference waves to find distances between the reference points and the transducers on the probe, thus to determine the position coordinates.

24. A method according to claim 18, wherein emitting and receiving the waves comprise emitting and receiving the waves while the probe is held substantially stationary at a single location in the heart, and wherein reconstructing the three-dimensional geometrical map comprises reconstructing the shape of the surface of the heart based substantially only on the waves received at the single location.

25. A method according to claim 18, wherein reconstructing the geometrical map comprises determining, responsive to the times of flight, distances from the transducers along the probe to corresponding points on the surface of the heart generally opposite the points along the probe, and combining the determined distances so as to reconstruct the shape of the surface of the heart.

26. A method according to claim 25, wherein determining the distances comprises distinguishing the waves received at the transducers along the probe after one reflection from the surface of the heart from the waves received after multiple reflections, and rejecting the waves received after the multiple reflections.

27. A method according to claim 25, wherein the heart has a wall, and the surface comprises an inner surface of the wall and an outer surface of the wall, and wherein determining the distances comprises distinguishing the waves received at the transducers along the probe after reflection from the inner surface from the waves received after reflection from the outer surface.

28. A method according to claim 27, wherein reconstructing the geometrical map of the surface of the heart comprises determining a thickness of the wall by comparing the times of flight of the waves received after reflection from the inner surface to those of the waves received after reflection from the outer surface.

29. A method according to claim 18, and comprising analyzing the received waves to detect a spectral shift therein, so as to determine, responsive to the spectral shift, a velocity of motion of the surface.

30. A method according to claim 29, wherein reconstructing the geometrical map of the surface of the heart comprises generating a map of the heart that includes an indication of the velocity of motion of different areas of the surface.

31. A method according to claim 18, and comprising sensing electrical activity in the heart using electrical sensors on the probe.

32. A method according to claim 31, wherein reconstructing the geometrical map of the surface of the heart comprises superimposing an indication of the electrical activity on the reconstructed three-dimensional geometrical map of the surface of the heart.

33. A method according to claim 31, wherein sensing the electrical activity comprises detecting varying electrical potentials at the surface of the heart substantially without contact between the electrical sensors on the probe and the surface.

34. Apparatus for rapid reconstruction of a beating heart comprising:

a catheter having an array of ultrasonic transducers longitudinally arrayed along a surface of the catheter;

a console having signal processing circuits operatively connected to the catheter, the signal processing circuits generating an actuation signal to at least one of the ultrasonic transducers of the array for emitting an ultrasonic pulse to a surface of the heart, the ultrasonic pulse emitted to the surface of the heart having a frequency and a duration that permits the ultrasonic pulse to be reflected back to the ultrasonic transducers of the array from the surface of the heart, the ultrasonic transducers of the array generating an electrical signal to the signal processing circuits, the signal processing circuits determining time of flight information of the ultrasonic pulse, the time of flight of information being collected by the signal processing circuits during a period of time shorter than a single heart beat, the signal processing circuits reconstructing a geometrical shape of the surface of the heart based on the time of flight information for the period of time shorter than a single heart beat.

35. Apparatus according to claim 34, wherein the array of ultrasonic transducers comprises at least 10 ultrasonic transducers.

36. Apparatus according to claim 35, wherein the array of ultrasonic transducers comprises between 10 to 20 ultrasonic transducers.

37. Apparatus according to claim 36, wherein the frequency of the ultrasonic pulse is between 5–9 MHz.

38. Apparatus according to claim 37, wherein the duration of the ultrasonic pulse is 1 $\mu$s.

* * * * *